United States Patent
Sun et al.

(10) Patent No.: US 7,560,095 B2
(45) Date of Patent: Jul. 14, 2009

(54) CANCER SPECIFIC MONOCLONAL ANTIBODIES

(75) Inventors: Le Sun, Ellicott City, MD (US); Ginette Serrero, Ellicott City, MD (US); Joe Corvera, Baltimore, MD (US); Yudong Hou, Shangdong (CN)

(73) Assignee: A & G Pharmaceutical, Inc., Columbia, MD (US)

( * ) Notice: Subject to any disclaimer, the term of this patent is extended or adjusted under 35 U.S.C. 154(b) by 107 days.

(21) Appl. No.: 10/554,321

(22) PCT Filed: Apr. 22, 2004

(86) PCT No.: PCT/US2004/012568

§ 371 (c)(1),
(2), (4) Date: Aug. 9, 2006

(87) PCT Pub. No.: WO2004/094612

PCT Pub. Date: Nov. 4, 2004

(65) Prior Publication Data

US 2007/0025911 A1 Feb. 1, 2007

Related U.S. Application Data

(60) Provisional application No. 60/464,350, filed on Apr. 22, 2003.

(51) Int. Cl.
*A61K 39/395* (2006.01)
*C07K 7/00* (2006.01)

(52) U.S. Cl. ............. 424/1.81; 424/1.49; 424/9.1; 424/9.6; 424/130.1; 424/141.1; 424/155.1

(58) Field of Classification Search ................ None
See application file for complete search history.

(56) References Cited

U.S. PATENT DOCUMENTS

| 5,972,337 A * | 10/1999 | Ceriani et al. ............ 424/185.1 |
| RE37,596 E | 3/2002 | Bosslet et al. |
| 7,183,384 B2 * | 2/2007 | Sun et al. .................... 530/386 |
| 2002/0137109 A1 | 9/2002 | Gelber |

* cited by examiner

*Primary Examiner*—Sheela J Huff
(74) *Attorney, Agent, or Firm*—Womble Carlyle Sandridge & Rice PLLC

(57) ABSTRACT

Novel monoclonal antibodies and binding fragments thereof specific to human breast cancer, lung cancer, colon cancer and other cancers. The monoclonal antibody does not bind to the cell surface of normal human tissues. The corresponding cancer-specific antigen or antigens with an apparent molecular weight of 40-52 130-200 kDa and polynucleotides encoding the antigen and the CDR regions of the antibody are also disclosed, as well as methods for diagnosis, prognosis and treatment of human breast cancer. The antibodies have tumor specificity and are useful for therapy, diagnosis, monitoring, detecting and imaging of cancers. The antibody-recognized cancer-specific surface antigens can serve as targets for detecting, diagnosing, inhibiting or killing cancer cells.

12 Claims, 2 Drawing Sheets

Breast cancer
Bladder cancer
Pancreas cancer
Figure 1: Immunohistochemistry of Various Human Tissues

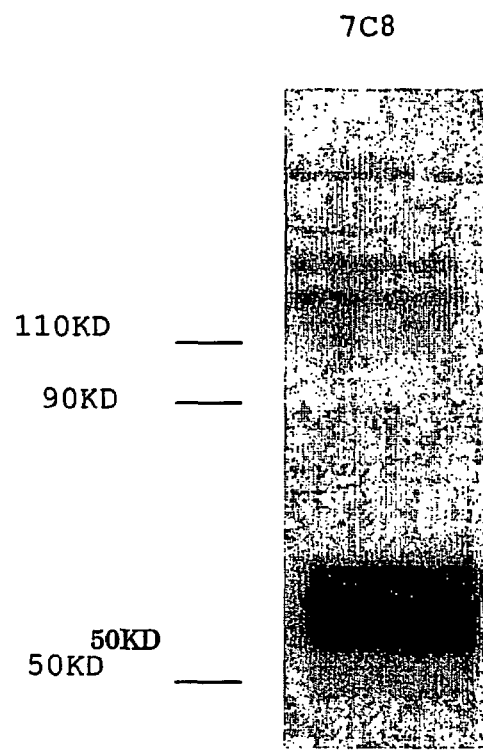
Figure 2: Western Blot Analysis of MDA-MB-468 with clone 7C8

CANCER SPECIFIC MONOCLONAL ANTIBODIES

This application claims the priority of U.S. Provisional Application No. 60/464,350, filed Apr. 22, 2003, the disclosure of which is expressly incorporated by reference herein.

FIELD OF THE INVENTION

This invention relates to immunology and cancer diagnosis and therapy. More particularly it relates to cancer cell surface specific proteins with molecular weight of about 40-52 kDa and about 130-200 kDa, and antibodies specific therefor, hybridomas that produce the antibody, immunochemicals comprising and derived from the antibody, and diagnostic methods that use the antibody. The invention also relates to the use of the antibodies alone or in combination with cytotoxic factor(s) in therapeutic methods.

BACKGROUND OF THE INVENTION

The use of antibodies as "magic bullets" to deliver toxins to cancer cells was proposed by Paul Ehrlich over a century ago, and the potential of targeted immunotherapy has since attracted the attention of generations of investigators. In 1975, with the development of the technology for producing monoclonal antibodies (MoAbs), (G. Kohler and C. Milstein, 1975, Nature, 256:495-497; see also Herzenberg and Milstein, Handbook of Experimental Immunology, ed. Weir (Blackwell Scientific, London), 1979, pp. 25.1-25.7), it seemed that successful antibody therapy was imminent. Early trials with monoclonal antibodies, however, revealed significant obstacles to their use in cancer therapy. Immune rejection of murine monoclonal antibodies, and low efficiencies were reported during initial clinical experience (Kwak et al., 1995, Clinical applications of monoclonal antibodies, In: Biologic Therapy of Cancer, Eds. V. T. DeVita, Jr., S. Hellman and S. A. Rosenberg, 2nd Ed., J. B. Lippincott Co., Philadelphia, Pa., pp. 553-565).

Ideally, antibody for cancer therapy should have a high affinity for its antigen, and an effective unconjugated antibody should work synergistically with the host's immune system effector mechanisms. Therapeutic antibodies that induce effector mechanisms such as antibody-dependent cellular cytotoxicity (ADCC) and complement-dependent cytolysis (Waldman et al., 1994, Ann. Oncol, 5 Suppl. 1:13-17) have the potential to provide targeted cancer therapy that is safe and effective without the use of potentially harmful conjugates such as toxins or radionuclides.

Nearly all monoclonal antibodies recognizing antigens on human cancer cells also bind to normal human cells expressing the same antigen (Jurcic et al., 1996, Cancer Chemotherapy and Biological Response Modifiers Annual, Eds. Pinedo et al. pp. 168-188). This cross-reactivity potentially compromises therapeutic effectiveness and raises issues of toxicity, leading to the continued interest in defining antigenic targets that are unique to tumor cells. It is therefore highly desirable to have cancer-specific antigens and prepare cancer specific antibodies. The identification of unique cancer antigens enables the design of selective immunotherapy for neoplastic diseases. The capacity to utilize a determinant that is exclusively expressed by cancer cells or tumor cells, but that is not present in normal cells and tissues, insures the targeting and elimination of the neoplastic cells, while insulating the viability and function of normal cells. For general background in this regard, please see Colcher et al., 1981, Proc. Natl. Acad. Sci. 78:3199-3203.

The process that leads to the discovery of unique cancer antigens is, however, long, tedious and elaborate, and entails an exhaustive weeding out of antigens expressed on both cancer or tumor cells and normal tissues (see e.g. U.S. Pat. Nos. 4,172,124 and 4,196,265). This is because malignant cells resemble their normal cell counterparts. Cancer cells often have "low visibility" to an individual's immune surveillance system, due to the fact that the majority of cancer antigens are self-antigens or auto-antigens that are also expressed by normal cells. Frequently, the cancer antigen is identical to the normal antigen although it is expressed at higher levels or endowed with a negligible mutation insufficient for its distinction from the self-antigen.

In spite of the above-mentioned obstacles, the present invention provides new and specific monoclonal antibodies which are immunoreactive with a cancer-specific cell surface antigen and which are useful in immunotherapy, diagnostic, imaging, monitoring and screening methodologies.

The monoclonal antibody 7C8 aides in the diagnosis, prognosis, and treatment of human cancers including breast and lung cancers. The antibody is reactive to only human cancer cells but not to apparently normal human tissues.

SUMMARY OF THE INVENTION

The invention generally relates to a monoclonal antibody, or binding fragment thereof that binds specifically to as antigens present in human breast cancer, human bladder cancer, and, human lung cancer. The antigens are (i) a polypeptides having an apparent molecular weight of about 150 kDa as determined by SDS-PAGE under reducing conditions; and (ii) absent from human breast, bladder and, lung tissue cells.

Preferably, the monoclonal antibody, or binding fragment thereof, of the present invention is produced by a hybridoma cell line designated "7C8." The hybridoma cell line designated "7C8." has been deposited with the American Type Culture Collection (ATCC), 10801 University Blvd., Manassas, Va. 20110-2209 on Mar. 28, 2006, under Patent Deposit Designation PTA-7448. All restrictions imposed by the depositor on the availability to the public of the deposited material will be irrevocably removed upon granting of the patent.

The monoclonal antibody or binding fragment thereof of the invention may be Fab fragments, $F(ab)_2$ fragments, Fab' fragments, $F(ab')_2$ fragments, Fd fragments, Fd' fragments or Fv fragments. It may also be an anti-idiotypic antibody.

Preferably, the antibody of the invention may be labeled with a detectable moiety, such as a fluorophore, a chromophore, a radionuclide, a chemiluminescent agent, a bioluminescent agent and an enzyme.

The present invention also provides a hybridoma cell line which produces a monoclonal antibody which binds specifically to an antigen present in human breast cancer, human bladder cancer, and human lung cancer, the antigen being (i) polypeptides having an apparent molecular weight of about 40-50, or 130-200 kDa as determined by SDS-PAGE under reducing conditions; and (ii) is absent from human breast, lung and bladder tissue cells. In a preferred embodiment, the hybridoma cell line according is the 7C8 cell line.

The present invention further provides an antibody-recognized surface antigen present in human breast cancer, human lung cancer, and human bladder cancer, the antigen being (i) polypeptides having an apparent molecular weight of about 42-50 or 130-200 kDa as determined by SDS-PAGE under reducing conditions; and (ii) absent from human breast, lung and bladder tissue cells. This antigen is recognized by monoclonal antibody produced by the hybridoma cell line 7C8.

In a further embodiment, the present invention provides a method of inhibiting or killing cancer cells, comprising: providing to a patient in need thereof the monoclonal antibody, or binding fragment thereof of the present invention, under conditions and in an amount sufficient for the binding to the cancer cells, thereby causing inhibition or killing of the cancer cells by the immune cells of the patient. Preferably, the method is for the treatment of breast cancer, lung cancer, or bladder cancer. The monoclonal antibody is preferably conjugated with a cytotoxic moiety, such as a chemotherapeutic agent, a photoactivated toxin, or a radioactive agent. Preferably, the cytotoxic moiety may be a Ricin A chain.

Also provided is a monoclonal antibody of the invention or a binding fragment thereof that is bound to a solid matrix.

The present invention further provides a method for localizing cancer cells in a patient, comprising: (a) administering to the patient a detectably-labeled monoclonal antibody of the invention, or binding fragment thereof; (b) allowing the detectably-labeled (e.g. radiolabeled; flurochrome labeled, or enzyme labeled, especially via ELISA) monoclonal antibody, or binding fragment thereof, to bind to the cancer cells within the patient; and (c) determining the location of the labeled monoclonal antibody or binding fragment thereof, within the patient. Also provided is a method of detecting the presence and extent of cancer in a patient, comprising: determining the level of the antigen in a sample of bodily fluid or a tissue section from the patient and correlating the quantity of the antigen with the presence and extent of the cancer disease in the patient. In preferred embodiment, the antigen is detected by (1) adding monoclonal antibody 7C8 to the sample or tissue section; (2) adding goat anti-mouse IgG antibody conjugated with peroxidase; (3) fixing with diaminobenzidene and peroxide, and (4) examining the sample or section, wherein reddish brown color indicates that the cells bear the antigen. According to the method, the effectiveness of a cancer treatment may be monitored by periodically measuring changes in the level of the antigen in a body fluid sample taken from a patient undergoing the therapy, and correlating the change in level of the antigen with the effectiveness of the therapy, wherein a lower level of antigen determined at a later time point relative to the level of antigen determined at an earlier time point during the course of therapy indicates effectiveness of the therapy for the cancer disease.

In another embodiment, the present invention relates to a method of diagnosing the presence of cancer in a patient, comprising: (a) measuring the levels of the antigen in cells, tissues, or body fluids of the patient; and (b) comparing the measured levels of the antigen of (a) with levels of the antigen in cells, tissues, or body fluids from a normal human control, wherein an increase in the measured levels of the antigen in the patient versus the normal control is associated with the presence of the cancer. Also provided is a method of imaging cancer in a patient, comprising administering to the patient the antibody, wherein the antibody is detectably labeled with paramagnetic ions or with a radioisotope.

The present invention further provides a pharmaceutical composition comprising the monoclonal antibody, or binding fragment thereof, according to the invention, and a pharmaceutically acceptable carrier, excipient, or diluent.

Still further provided are a method for downregulating HER2 receptor levels on an SK-BR-3 cell, comprising contacting the cell with a monoclonal antibody of the invention, and a method for sensitizing tumor cells to cisplatin or doxorubicin, comprising contacting the monoclonal antibody of the invention to the cell, wherein the antibody specifically binds to the extracellular domain of a HER2 receptor on the cell.

The present invention further relates to a polynucleotide encoding the antigen of the invention, and a polynucleotide encoding the monoclonal antibody of the invention.

Other aspects of the invention are apparent to those skilled in the art from the detailed description and examples below.

BRIEF DESCRIPTION OF THE DRAWINGS

FIG. 1 shows immunohistochemical staining of various human tissues using mAb 7C8.

FIG. 2 shows Western blot analysis of MDA-MB468 with clone 7C8.

DETAILED DESCRIPTION OF PREFERRED EMBODIMENTS

The present invention provides monoclonal antibodies and binding fragments thereof that specifically recognize and bind to a cell surface antigen expressed by various human tumor cells or cancer cells. The surface antigen are either exclusively present, or highly expressed, on the cancer cells, but are absent from, or less highly expressed or displayed, on developmentally related cells which serve as controls. The newly discovered cancer-specific surface antigens provide targets for therapeutic intervention in these cancers disease, as well as for diagnostic and cell purification purposes.

The present invention provides new monoclonal antibodies directed against cancer-specific antigen(s) expressed on human breast cancer cells. The monoclonal antibodies were characterized and found to bind specifically to antigens on the surface of breast cancer cells. In particular, a representative, exemplary monoclonal antibody was isolated, characterized and found to react specifically with surface proteins with apparent MW of about 40-52 or 130-200 KDa as determined by SDS-PAGE under reducing conditions. This MoAb was given the designation 7C8.

Another embodiment of the present invention relates to monoclonal antibodies, and binding fragments or portions thereof, which recognize the foregoing cell surface antigen. Thus, the present invention encompasses the specific monoclonal antibody 7C8, as well as antibodies, preferably monoclonal antibodies, and their binding fragments, having specificity for the above-described antigen present on human breast cancer, lung cancer and bladder cancer cells. Nonlimiting examples of antibody fragments or antigen bindable fragments that bind to epitopes on the antigen include the following: Fab fragments, F(ab)$_2$ fragments, Fab' fragments, fragments produced by F(ab) expression libraries, F(ab')$_2$ fragments, Fd fragments, Fd' fragments and Fv fragments. The antibodies may be human, or from animals other than humans, preferably mammals, such as rat, mouse, guinea pig, rabbit, goat, sheep, and pig. Preferred are mouse monoclonal antibodies and antigen-binding fragments or portions thereof. In addition, chimeric antibodies and hybrid antibodies are embraced by the present invention.

In accordance with the present invention, the monoclonal antibodies and binding fragments thereof may be characterized as those which are 1) produced from the hybridoma cell line 7C8; 2) antibodies that are capable of binding to the same antigenic determinant as does the monoclonal antibody produced by the hybridoma cell line; 3) binding fragments of the monoclonal antibody produced by the hybridoma cell line; or 4) binding fragments of a monoclonal antibody capable of binding to the same antigenic determinant as does the monoclonal antibody produced by the hybridoma cell lines.

The immunoglobulin isotype of the monoclonal antibodies of the present invention is IgG1.

According to the present invention, the monoclonal antibodies recognize specific cell surface antigens expressed by and present on human breast cancer, human lung cancer and human bladder cancer cells.

The surface antigen or antigens are polypeptide having an apparent molecular weight of about 40-52 or 130-200 KDa as determined by SDS-PAGE under reducing conditions. The cancer-specific antigen according to the present invention may contain conformational epitopes, whose recognition by the monoclonal antibody of the present invention may be dependent on the conformational nature of the antigen being intact and not denatured, degraded, or otherwise adversely affected. The cancer-specific antigen may be glycosylated, and different degree of glycosylation causes it to migrate as multiple bands on an SDS-PAGE gel. The antigen may be post-translationally processed, and both its precursor and processed fragments show up on the Western Blot. Alternatively, the antigen may be degraded and the degraded fragments retain their reactivity to the monoclonal antibody. Another probability is that the cancer cells have multiple antigen proteins that shows the same epitope that is recognized by the monoclonal antibody.

The present invention further provides hybridoma cell lines that produce monoclonal antibodies that specifically bind to the antigen. Methods for preparing hybridoma cell lines are well known in the art. Accordingly, any technique or protocol that results in the production of homogeneous populations of antibody molecules to a specific antigen, preferably monospecific antibody molecules, e.g., monoclonal antibodies, by continuous cell lines in culture may be used. Such techniques include, but are not limited to, the hybridoma technique developed by Kohler and Milstein (1975, supra), the trioma technique, the human B-cell hybridoma technique (Kozbor et al., 1983, Immunology Today, 4:72; Cote et al., 1983, Proc. Nat'l Acad. Sci. USA, 80:2026-2030), as well as the Epstein Barr Virus (EBV)-hybridoma technique to produce human monoclonal antibodies (Cole et al., 1985, In: Monoclonal Antibodies and Cancer Therapy, Alan R. Liss, Inc., pp. 77-96). Such antibodies may be of any immunoglobulin class, including IgM, IgG, IgE, IgA and IgD, or any subclass thereof Hybridoma cells may be cultured in vivo or in vitro according to established methods.

In a further aspect, monoclonal antibodies can be produced in germ-free animals utilizing the technology described in International Patent Application No. WO 98/02545. Also suitable for use in the present invention are hybrid antibodies, chimeric antibodies and humanized antibodies (e.g., U.S. Pat. No. 5,585,089 to Queen et al.). Antibodies, such as hybrid or chimeric antibodies having human components, or humanized antibodies, are more preferable for use in therapies of human diseases or disorders than xenogenic antibodies, because the human or humanized antibodies are much less likely than xenogenic antibodies to induce an immune response, particularly an allergic response, when introduced into a human host.

In addition, techniques developed for the production of chimeric antibodies (Morrison et al., 1984,.Proc. Natl. Acad. Sci. USA, 81:6851-6855; Neuberger et al., 1984, Nature, 312:604-608, Takeda et al., 1985, Nature, 314:452-454) by splicing the genes (see below) from a mouse antibody molecule of appropriate antigen specificity together with genes from a human antibody molecule of appropriate biological activity are suitable for use in the present invention.

Further, according to the present invention, the techniques described for the production of single chain antibodies (e.g., U.S. Pat. Nos. 5,476,786 and 5,132,405 to Huston; Huston et al., 1988, Proc. Natl. Acad. Sci. USA, 85:5879-5883; U.S. Pat. No. 4,946,778 to Ladner et al.; Bird, 1988, Science, 242:423-426 and Ward et al., 1989, Nature, 334:544-546) can be adapted to produce cancer-specific single chain antibodies. Single chain antibodies are formed by linking the heavy and light immunoglobulin chain fragments of the Fv region via an amino acid bridge, resulting in a single chain polypeptide. Univalent antibodies are also embraced by the present invention. In addition, techniques for the construction of Fab expression libraries (Huse et al., 1989, Science, 246:1275-1281) are suitable for use in this invention to allow the rapid and easy identification of monoclonal antibody Fab fragments, or derivatives or analogs, having an altered, preferably increased, specificity.

Antibody fragments containing the idiotype of the antibody of the present invention, can be produced by known techniques (Greenspan and Bona, 1993, FASEB J., 7(5):437-444 and Nissinoff, 1991, J. Immunol., 147(8):2429-2438). For example, such fragments include, without limitation, the $F(ab)_2$ fragment, which can be produced by pepsin digestion of the intact antibody molecule; the Fab' fragment, which can be produced by reducing the disulfide bridges of the $F(ab')_2$ fragments, and the Fab fragments, which can be generated by treating the intact antibody molecule with the enzyme papain and a reducing agent.

It is also envisioned that antibodies can be elicited in an animal host by immunization with cancer cell-derived immunogenic components, or can be formed by in vitro immunization (sensitization) of immune cells. The antibodies can also be produced in recombinant systems in which the appropriate cell lines are transformed, transfected, infected or transduced with appropriate antibody-encoding DNA. Alternatively, the antibodies can be constructed by biochemical reconstitution of purified heavy and light chains.

Using the aforementioned types of antibodies or fragments, cells displaying the specifically recognized surface antigen(s), or the antigen(s) themselves, or an immunogenic fragment or portion thereof, can be detected in a test sample by chromatography on antibody-conjugated solid-phase matrices or supports (see E. Harlow and D. Lane, 1999, Using Antibodies: A Laboratory Manual, Cold Spring Harbor Laboratory, Cold Spring Harbor, N.Y.), or by immunoassays. Preferred are antibodies that specifically recognize and bind to the antigen(s) of the present invention.

Nucleic Acid Molecules Encoding Antibodies of the Invention

The present invention also provides for nucleic acid molecules encoding an antibody of the invention (including molecules comprising, or alternatively consisting of, antibody fragments or variants thereof). In a specific embodiment, a nucleic acid molecule of the invention encodes an antibody (including molecules comprising, or alternatively. consisting of, antibody fragments or variants thereof), comprising, or alternatively consisting of, a $V_H$ domain having an amino acid sequence of any one of the $V_H$ domains of a heavy chain expressed by a cell line expressing an antibody of the invention, and a $V_L$ domain having an amino acid sequence of a light chain expressed by an cell line expressing an antibody of the invention. Preferably, the cell line is 7C8.

In order to isolate the $V_H$ and $V_L$ domains from the hybridoma cell lines, PCR primers including $V_H$ or $V_L$ nucleotide sequences, may be used to amplify the expressed $V_H$ and $V_L$ sequences contained in total RNA or MRNA isolated from hybridoma cell line 7C8. Briefly, RNA is isolated from the cell lines and used as a template for RT-PCR designed to amplify the $V_H$ and $V_L$ domains of the antibodies expressed by the 7C8 cell line. Cells may be lyzed and total RNA extracted. cDNA may be synthesized, according to methods well-known in the art, from 1.5-2.5 µg of RNA using reverse transciptase and random hexamer primers. cDNA is then used as a template for PCR amplification of $V_H$ and $V_L$ domains. Alternatively, total RNA is isolated and then the first strand of cDNA synthesized by reverse-transcription reaction using the $d(T)_{17}$ primer.

Primers used to amplify $V_H$ and $V_L$ genes may be obtained by methods well-known to those skilled in the art. For example, the 5' primers for amplification of mouse V genes may be synthesized according to Coloma et al., (1992, J. Immunol. Methods 152:89-104), and designed to hybridize to partially conserved sequences in the leader regions of $V_H$ and $V_L$. The 3' primer for $V_L$ genes was located at V-C junction of $V_L$. The 3' primer for $V_H$ genes may be designed on conserved sequences located at the boundary of $V_H$ and CH1. Alternatively, Vk1FOR and Vk1BACK for $V_L$ chain, VH1FOR and VH1BACK for $V_H$ chain according to Orlandi et al. (1989, Cloning immunoglobulin variable domains for expression by the polymerase chain reaction. *Proc. Natl Acad Sci. USA* 86, 3833-3837) may be used. The PCR amplification may be in a volume of 100 µl and performed with a typical cycle of denaturation at 94° C. for 1 min, annealing at 30-42° C. for 1.5 min, and elongation at 72° C. for 1.5 min.

The PCR products may then be cloned using vectors, for example, which have a PCR product cloning site consisting of a 5' and 3' single T nucleotide overhang, that is complementary to the overhanging single adenine nucleotide added onto the 5' and 3' end of PCR products by many DNA polymerases used for PCR reactions. The PCR products may also be gel-purified and ligated into cloning vector pBluscript KS (Stratagene) at the EcoRV site. The $V_H$ and $V_L$ domains can then be sequenced using conventional methods known in the art. A comparison of the sequences of the $V_H$ and $V_L$ domains from AR20.5 (Ab1) and AR42.1 (Ab2) with the Kabat protein database (Kabat, et al., 1991, *Sequence of Proteins of Immunological Interest*, 5th ed., NIH publication No. 91-3242, U.S. Department of Health and Human Services, Bethesda) may be used to determine the Complementary Determining Region (CDR) sequences for the antibody gene.

Sequences encoding the cDNAs or genomic clones for the particular antibodies can be used for transformation of a suitable mammalian or nonmammalian host cells or to generate phage display libraries, for example. Additionally, polypeptide antibodies of the invention may be chemically synthesized or produced through the use of recombinant expression systems.

The cloned $V_H$ and $V_L$ genes may be placed into one or more suitable expression vectors. By way of non-limiting example, PCR primers including $V_H$ or $V_L$ nucleotide sequences, a restriction site, and a flanking sequence to protect the restriction site may be used to amplify the $V_H$ or $V_L$ sequences. Utilizing cloning techniques known to those of skill in the art, the PCR-amplified $V_H$ domains may be cloned into vectors expressing the appropriate immunoglobulin constant region, e.g., the human IgG1 or IgG4 constant region for $V_H$ domains, and the human kappa or lambda constant regions for kappa and lambda $V_L$ domains, respectively. Preferably, the vectors for expressing the $V_H$ or $V_L$ domains comprise a promoter suitable to direct expression of the heavy and light chains in the chosen expression system, a secretion signal, a cloning site for the immunoglobulin variable domain, immunoglobulin constant domains, and a selection marker such as neomycin. The $V_H$ and $V_L$ domains may also be cloned into a single vector expressing the necessary constant regions. The heavy chain conversion vectors and light chain conversion vectors are then co-transfected into cell lines to generate stable or transient cell lines that express full-length antibodies, e.g., IgG using techniques known to those of skill in the art (See, for example, Guo et al., J. Clin. Endocrinol. Metab. 82:925-31 (1997), and Ames et al., J. Immunol. Methods 184:177-86 (1995) which are herein incorporated in their entireties by reference).

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well known in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds an antigen of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

For some uses, such as for in vitro affinity maturation of an antibody of the invention, it may be useful to express the $V_H$ and $V_L$ domains of the heavy and light chains of one or more antibodies of the invention as single chain antibodies or Fab fragments in a phage display library. For example, the cDNAs encoding the $V_H$ and $V_L$ domains of one or more antibodies of the invention may be expressed in all possible combinations using a phage display library, allowing for the selection of $V_H/V_L$ combinations that bind to the cancer-specific antigen(s) of the invention, with preferred binding characteristics such as improved affinity.

In phage display methods, functional antibody domains are displayed on the surface of phage particles which carry the polynucleotide sequences encoding them. In particular, DNA sequences encoding $V_H$ and $V_L$ domains are amplified from animal cDNA libraries (e.g., human or murine cDNA libraries of lymphoid tissues) or synthetic cDNA libraries. The DNA encoding the $V_H$ and $V_L$ domains are joined together by an scFv linker by PCR and cloned into a phagemid vector (e.g., pCANTAB 6 or pComb 3 HSS). The vector is electroporated in *E. coli* and the *E. coli* is infected with a helper phage. Phages used in these methods are typically filamentous phage including fd and M13 and the $V_H$ and $V_L$ domains are usually recombinantly fused to either the phage gene III or gene VIII. Phages expressing an antigen binding domain that binds to an antigen of interest can be selected or identified with the antigen, e.g., using labeled antigen or antigen bound or captured to a solid surface or bead. Examples of phage display methods that can be used to make the antibodies of the present invention include, but are not limited to, those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); and Burton et al., Advances in Immunology 57:191-280(1994).

The antibodies of the invention can be produced by any method known in the art for the synthesis of antibodies, in particular, by chemical synthesis, or by intracellular immunization (i.e., intrabody technology). Methods of producing antibodies also include hybridoma technology, EBV transformation, and other methods discussed herein as well as through the use recombinant DNA technology, as discussed below.

Recombinant expression of an antibody of the invention, or fragment, derivative, variant or analog thereof, (e.g., a heavy or light chain of an antibody of the invention or a single chain antibody of the invention), involves construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody-encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the antibody molecules of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3, NSO cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *E. coli*, and more preferably, eukaryotic cells, especially for the expression of whole recombinant antibody molecule, are used for the expression of a recombinant antibody molecule.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen, Protein A/G chromatography, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The antibodies can be employed to prepare antigen-antibody affinity columns, which may be used for the purification of the antigen. For example, gel supports or beads can be activated with various chemical compounds, e.g., cyanogen bromide, N-hydroxysuccinimide esters, and antibodies can be bound thereto. More particularly and by way of example, antibodies can be added to Affigel-10 (Biorad), a gel support which is activated with N-hydroxysuccinimide esters, such that the antibodies form covalent linkages with the agarose gel bead support. The antibodies are then coupled to the gel via amide bonds with a spacer arm. The remaining activated esters are then quenched with ethanolamine HCl, 1 M, pH 8. The column is washed with water, followed by 0.23 M glycine HCl, pH 2.6, to remove any non-conjugated antibody or extraneous protein. The column is then equilibrated in phosphate buffered saline (PBS), (pH 7.3) with appropriate detergent, and the sample materials, i.e., cell culture supernatants or cell extracts, for example, containing the cancer-specific antigens (e.g., prepared using appropriate membrane solubilizing surfactants) are slowly passed over the column. The column is washed with PBS/surfactant until the optical density falls to background. The protein is then eluted from the column with 0.23 M glycine-HCl, pH 2.6/surfactant. The purified antigens is then dialyzed against PBS/surfactant.

In another embodiment, the present invention embraces the isolated cancer cell-specific antigen(s), as described herein and as recognized and bound by the monoclonal antibody 7C8. In particular, the invention embraces the approximately 40-52 KDa protein antigen. Further embraced by the present invention are cancer cell-specific antigens comprising an epitope recognized by the monoclonal antibody 7C8. The cell surface glycoproteins comprising the recognized conformational epitope are substantially not present on normal cells.

For example, the 40-52 kDa antigen of the present invention may be identified on a preparatory 2-D gel using the 7C8 monoclonal antibody, and purified. The purified protein may then be sequenced with one of many well-known and commercially available techniques. The partial amino acid sequence may be used to design degenerative primers or probes, which can be used to clone from a suitable cancer cell the gene or cDNA that encodes the antigen.

Another aspect of the present invention relates to therapeutic methods for the treatment of cancer patients, particularly individuals afflicted with cancers involving cells displaying the 40-52 kDa cancer-specific antigen, more particularly, breast cancer, colon cancer, esophagus cancer, liver cancer, lung cancer and bladder cancer cells.

The therapeutic methods encompassed by the present invention involve primary tumors or cancers, as well as metastases. As an example, a method for inhibiting or killing cancer cells comprises administering to a patient one or more of the monoclonal antibodies having specificity for the cancer cells, or a binding fragment thereof, as described above, under conditions sufficient for the binding of the monoclonal antibody, or binding fragment, to tumor or cancer cells in the patient. The binding of antibodies, or their binding fragments, to the tumor cells or cancer cells induces the inhibiting or killing of the cells by the patient's immune cells. The above described method employs the antibodies or their binding fragments without modification, relying on the binding of the antibodies to the surface of the cancer cells in situ to stimulate and induce an immune response and attack by autologous immune cells thereon.

Such antibody-mediated treatment or therapy may also be accompanied by other treatments that are directed to tumor or cancer cells, for example, radiation, chemotherapy, and the like, as well as by adjunctive therapies to enhance the immune system's attack on the opsonized cancer or tumor cells following the above-described treatment/therapy procedure(s).

More specifically, a growth factor, lymphokine, or cytokine may be co-administered with one or more of the monoclonal antibodies, for example, erythropoietin and/or GM-CSF (granulocyte/macrophage colony-stimulating factor), to stimulate white blood cells and support the immunocompetence status of the patient. In addition, chimeric or fusion antibodies, or other recombinant antibodies of the present invention may be used in therapies and treatment. For example, a fusion protein molecule comprising at least the antigen-binding region of an antibody of the invention joined to at least a functionally active or bioactive portion of a second protein having anti-tumor or cancer effects, e.g., a lymphokine or oncostatin, may be used to treat the cancer, particularly, in vivo. Moreover, a chimeric antibody can be prepared, wherein the antigen binding portion or site is joined to a human Fc molecule of an immunoglobulin, e.g., IgG1, to promote antibody-dependent mediated cytotoxicity or complement-mediated cytotoxicity. Recombinant techniques and protocols as known and practiced in the art (e.g., U.S. Pat. No. 4,474,893 to Reading) may be used to construct bispecific or bifunctional chimeric antibodies wherein one of the binding specificities is that of the antibody according to the present invention.

In another aspect, the present invention comprises therapeutic methods utilizing the described monoclonal antibodies, or binding fragments thereof, to which a cytotoxic agent has been bound, affixed or coupled. The binding of the cytotoxic antibodies or binding fragments thereof, to the tumor or cancer cells inhibits the growth of the cells and optimally kills the cells. Examples of suitable cytotoxic agents include chemotherapeutic compounds, a drug (e.g., Garnett and Baldwin, 1986, Cancer Res., 46:2407-24112), a prodrug, enzymes, a photoactivated toxin, or a radioactive agent. Cytotoxic agents include, but are not limited to, ricin A chain, abrin A chain, modeccin A chain, gelonin, melphalan, bleomycin, adriamycin, daunomycin, or pokeweed antiviral proteins (PAP, PAPII, or PAP-S).

One of ordinary skills in the art will realize that there are numerous radionuclides and chemocytotoxic agents that can be coupled to cancer-specific antibodies by well-known techniques and delivered to a site to specifically destroy tumor cells and tissue. (See e.g. U.S. Pat. No. 4,542; and Pastan et al., 1986, Cell, 47:641-648). Examples of photoactivated toxins include dihydropyridine- and omega-conotoxin (Schmidt et al., 1991, J. Biol. Chem., 266(27):18025-18033). Nonlimiting examples of imaging and cytotoxic reagents that are suitable for use include $^{125}$I, $^{123}$I, $^{111}$In (e.g., Sumerdon et al., 1990, Nucl. Med. Biol., 17:247-254), $^{99m}$Tc, $^{32}$P, $^{3}$H and $^{14}$C; fluorescent labels such as fluorescein and rhodamine; chemiluminescent labels such as luciferin, and paramagnetic ions for use in magnetic resonance imaging (Lauffer et al., 1991, Magnetic Resonance in Medicine, 22:339-342). Antibodies can be labeled with such reagents using protocols and techniques known and practiced in the art. See, for example, Wenzel and Meares, Radioimmunoimaging and Radioimmunotherapy, Elsevier, New York, 1983; Colcer et al., 1986, Meth. Enzymol., 121:802-816; and Monoclonal Antibodies for Cancer Detection and Therapy, Eds. Baldwin et al., Academic Press, 1985, pp. 303-316, for techniques relating to the radiolabeling of antibodies. Yttrium-90 labeled monoclonal antibodies have been described for maximizing the dose delivered to the tumor or cancer cells and/or tissue, while limiting toxicity to normal tissues (e.g., Goodwin and Meares, 1997, Cancer Supplement, 80:2675-2680). Other cytotoxic radionuclides including, but not limited to, Copper-67 ($^{67}$Cu), Iodine-131 ($^{131}$I) and Rhenium-186 can also be used for labeling monoclonal antibodies.

The detectable/detecting label used is selected according to the imaging modality to be used. For example, radioactive labels, such as Indium-111 ($^{111}$In), Technetium-99m ($^{99m}$Tc), or Iodine 131, can be used for planar scans or for single photon emission computed tomography (SPECT). Also, positron-emitting labels such as Fluorine-19 can be used in positron emission tomography (PET). Paramagnetic ions, such as Gadlinium(III) or Manganese(II) can be used in magnetic resonance imaging (MRI). The monoclonal antibodies can also be labeled with radio-opaque labels for the visualization of cancer cells after injection, for example, by X-ray, CATscan, or MRI. In particular, for lung cancers, localization of the label within the lung, or external to the lung, permits the determination of the spread of the disease. The amount of label that is present and detectable within the lung, for example, allows the determination of the presence or absence of cancer or tumor in the lung.

Other covalent and non-covalent modifications of the monoclonal antibodies, or their binding fragments, as described herein are further encompassed for use in the present invention. Such modifications are meant to include agents which are co-administered with, or are administered subsequent to, the administration of the antibody(ies), or fragments thereof, to induce or stimulate growth inhibition or killing of the cells to which the antibody(ies) or fragments bind. For example, immunotoxins conjugated to monoclonal antibodies have been found to be efficacious in animal models. The conjugation of MoAbs with ribosome-inactivating proteins (e.g., ricin A-chain, ricinus agglutinin, or viscumin) or photoinactivating agents has been described (see, e.g., D. B. Papkovskii et al., 1990, Biomed. Sci., 1(4):401-406). In addition, pokeweed antiviral protein (PAP) has the ability to disrupt anti-apoptotic complexes or inhibit protein synthesis within the target cell, ultimately resulting in the death of the cell. Further, a number of small molecules that inhibit tyrosine kinases can be specifically targeted to cancer cells as growth factor conjugates and which can be administered with the monoclonal antibodies, or fragments thereof, according to the present invention.

In a related embodiment of the present invention, the monoclonal antibodies according to this invention can be used for immunotherapy, either coupled or uncoupled with a therapeutic agent. These therapeutic agents can be coupled either directly or indirectly to the described monoclonal antibodies, using techniques routinely practiced in the art. One example of indirect coupling is by the use of a spacer moiety. Spacer moieties, in turn, can be either insoluble or soluble (Dieher et al., 1986, Science, 231:148) and can be selected to enable drug release from the monoclonal antibody molecule at the target site. Examples of therapeutic agents which can be coupled to the monoclonal antibodies of the invention for anti-cancer immunotherapy are drugs, radioisotopes, lectins, and toxins.

The drugs with which can be conjugated to the monoclonal antibodies of the present invention include non-proteinaceous as well as proteinaceous compounds. The term "non-proteinaceous drugs" encompasses compounds classically referred to as drugs, for example, mitomycin C, daunorubicin, and vinblastine. The proteinaceous drugs with which the monoclonal antibodies of the invention can be labeled include immunomodulators and other biological response modifiers.

The term "biological response modifiers" is meant to encompass substances that are involved in modifying the immune response in such manner as to enhance the destruction of the antigen-bearing tumor for which the monoclonal antibodies of the invention is specific. Examples of immune response modifiers include such compounds as lymphokines. Lymphokines include tumor necrosis factor, interleukins, e.g., IL1 through IL15, lymphotoxin, macrophage activating factor (MAF), migration inhibition factor (MIF), colony stimulating factor (CSF), and interferon. Interferons with which the monoclonal antibodies of the invention can be labeled include alpha-interferon, beta-interferon and gamma-interferon and their subtypes.

In using radioisotopically conjugated monoclonal antibodies of the invention for immunotherapy, certain isotopes may be more preferable than others depending on such factors as leukocyte distribution as well as isotope stability and emission. If desired, the tumor cell distribution can be evaluated by the in vivo diagnostic techniques described above. Depending on the malignancy, some emitters may be preferable to others. In general, alpha and beta particle-emitting radioisotopes are preferred in immunotherapy. For example, if an animal has solid tumor foci, as in a carcinoma, a high energy beta emitter capable of penetrating several millimeters of tissue, such as $^{90}Y$, may be preferable. On the other hand, if the malignancy consists of simple target cells, as in the case of leukemia, a shorter range, high energy alpha emitter, such as $^{212}Bi$, may be preferable. Examples of radioisotopes which can be bound to the monoclonal antibodies of the invention for therapeutic purposes are $^{125}I$, $^{131}I$, $^{90}Y$, $^{67}Cu$, $^{212}Bi$, $^{211}At$, $^{212}Pb$, $^{47}Sc$, $^{109}Pd$, and $^{188}Re$.

Lectins are proteins, usually isolated from plant material, which bind to specific sugar moieties. Many lectins are also able to agglutinate cells and stimulate lymphocytes. Ricin is a toxic lectin that has been used immunotherapeutically. This is preferably accomplished by binding the alpha-peptide chain of ricin, which is responsible for toxicity, to the antibody molecule to enable site specific delivery of the toxic effect.

Toxins are poisonous substances produced by plants, animals, or microorganisms that, in sufficient dose, are often lethal, especially to cells in the vicinity. Diphtheria toxin (DT), a substance produced by *Corynebacterium diphtheria*, can be used therapeutically. DT consists of an alpha and beta subunit which under proper conditions can be separated. The toxic alpha component can be bound to an antibody and used for site specific delivery to a cell bearing an antigen for which the monoclonal antibodies of the invention are specific. Other therapeutic agents which can be coupled to the monoclonal antibodies of the invention are known, or can be easily ascertained, by those of ordinary skill in the art.

The labeled or unlabeled monoclonal antibodies of the present invention can also be used in combination with therapeutic agents such as those described above. Especially preferred are therapeutic combinations comprising the monoclonal antibody of the invention and immunomodulators and other biological response modifiers. Thus, for example, the monoclonal antibodies of the invention can be used in combination with alpha-interferon. This treatment method enhances monoclonal antibody targeting of cancers by increasing the expression of monoclonal antibody reactive antigen by the cancer cells (Greiner et al., 1987, Science, 235:895). Alternatively, the monoclonal antibodies of this invention may be used, for example, in combination with gamma-interferon to activate and increase the expression of Fc receptors by effector cells, which, in turn, results in an enhanced binding of the monoclonal antibody to the effector cell and killing of target tumor cells. Those of skill in the art will be able to select from the various biological response modifiers to create a desired effector function which enhances the efficacy of the monoclonal antibodies of the invention.

When the monoclonal antibodies of the present invention are used in combination with various therapeutic agents, the administration of the monoclonal antibody and the therapeutic agent usually occurs substantially contemporaneously. The term "substantially contemporaneously" means that the monoclonal antibody and the therapeutic agent are administered reasonably close together with respect to time. Usually, it is preferred to administer the therapeutic agent before the monoclonal antibody. For example, the therapeutic agent can be administered 1 to 6 days before the monoclonal antibody. The administration of the therapeutic agent can be daily, or at any other interval, depending upon such factors, for example, as the nature of the tumor, the condition of the patient and the half-life of the agent.

Using the monoclonal antibodies of the present invention, it is possible to design therapies combining all of the characteristics described herein. In a given situation, it may be desirable to administer a therapeutic agent, or agents, prior to the administration of the monoclonal antibodies of the invention, in combination with effector cells and the same, or different, therapeutic agent or agents. For example, it may be desirable to treat patients with malignant disease by first administering gamma-interferon and interleukin-2 daily for 3 to 5 days, and on day 5 administer the monoclonal antibody of the invention in combination with effector cells, as well as gamma-interferon, and interleukin-2.

It is also possible to utilize liposomes with the monoclonal antibodies of the present invention in their membranes to specifically deliver the liposome to the area of the tumor expressing SCLC-specific antigens. These liposomes can be produced such that they contain, in addition to monoclonal antibody, immunotherapeutic agents, such as those described above, which would then be released at the tumor site (e.g., Wolff et al., 1984, Biochem. et Biophys. Acta, 802:259).

The dosage ranges for the administration of the monoclonal antibodies of the invention are those large enough to produce the desired effect in which the symptoms of the malignant disease are ameliorated. The dosage should not be so large as to cause adverse side effects, such as unwanted cross-reactions, anaphylactic reactions, and the like. Generally, the dosage will vary with the age, condition, sex and extent of disease of the patient and can be determined by one of skill in the art. The dosage can be adjusted by the individual physician in the event of any complication. Dosage can vary from about 0.1 mg/kg to about 2000 mg/kg, preferably about 0.1 mg/kg to about 500 mg/kg, in one or more dose administrations daily, for one or several days.

Generally, when the monoclonal antibodies of the present invention are administered conjugated with therapeutic agents, lower dosages, comparable to those used for in vivo immunodiagnostic imaging, can be used. The monoclonal antibodies of the invention can be administered parenterally by injection or by gradual perfusion over time. The monoclonal antibodies of the invention can be administered intravenously, intraperitoneally, intramuscularly, subcutaneously, intracavity, or transdermally, alone or in combination with effector cells. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

As mentioned above, anti-idiotypic monoclonal antibodies to the antibodies according to the present invention may be used in therapies and treatments in active tumor immunization and tumor therapy (See, Larson et al., 1986, "Therapeutic applications of radiolabeled antibodies: Current situation and prospects", Int. J. Rad. Appl. Instrum., B).

The monoclonal antibodies, or binding fragments thereof, according to the present invention, may be used to quantitatively or qualitatively detect the presence of the cancer-specific antigen on cancer cells. This can be achieved, for example, by immunofluorescence techniques employing a fluorescently labeled antibody, coupled with light microscopic, flow cytometric, or fluorometric detection. In addition, the antibodies, or binding fragments thereof, according to the present invention may additionally be employed histologically, as in immunofluorescence, immunoelectron microscopy, or non-immuno assays, for in situ detection of the cancer-specific antigen on cells, such as for use in monitoring, diagnosing, or detection assays.

In situ detection may be accomplished by removing a histological specimen from a patient, and applying thereto a labeled antibody according to this invention. The antibody, or antigen-binding fragment thereof, is preferably applied by overlaying the labeled antibody or fragment onto the biological sample. Through the use of such a procedure, it is possible to determine not only the presence of the antigen, or conserved variants, or peptide fragments, but also its distribution in the examined tissue. The ordinarily skilled in the art will readily recognize that any of a wide variety of histological methods, e.g., staining procedures, can be modified in order to achieve such in situ detection.

Immunoassay and other assays for the antigen, or conserved variants, or peptide fragments thereof, typically comprise incubating a sample, such as a biological fluid, tissue extract, freshly harvested cells, or lysates of cells that have been incubated in cell culture, in the presence of a detectably-labeled antibody that recognizes the antigen, conserved variants, or peptide fragments thereof, such as the cancer-specific monoclonal antibodies, or binding fragments thereof, of the present invention. Thereafter, the bound antibody, or binding fragment thereof, is detected by a number of techniques well known in the art.

The biological sample may be brought into contact with, and immobilized onto, a solid phase support or carrier, such as nitrocellulose, or other solid support or matrix, which is capable of immobilizing cells, cell particles, membranes, or soluble proteins. The support may then be washed with suitable buffers, followed by treatment with the detectably-labeled antibody. The solid phase support may then be washed with buffer a second time to remove unbound antibody. The amount of bound label on the solid support may then be detected by conventional means. Accordingly, in another embodiment of the present invention, compositions are provided comprising the monoclonal antibodies, or binding fragments thereof, bound to a solid phase support, such as described herein.

By solid phase support or carrier or matrix is meant any support capable of binding an antigen or an antibody. Well-known supports or carriers include glass, plastic, nylon wool, polystyrene, polyethylene, polypropylene, dextran, nylon, amylases, films, resins, natural and modified celluloses, polyacrylamides, agarose, alumina gels, gabbros, and magnetite. The nature of the carrier can be either soluble to some extent, or insoluble for the purposes of the present invention. The support material may have virtually any possible structural configuration as long as the coupled molecule is capable of binding to an antigen or antibody. Thus, the support configuration may be spherical, as in a bead, cylindrical, as in the inside surface of a test tube, or the external surface of a rod. Alternatively, the surface may be flat, such as a sheet, film, test strip, stick, and the like. In addition, the solid support is preferably inert to the reaction conditions for binding and may have reactive groups, or activated groups, in order to attach the monoclonal antibody, a binding fragment, or the binding partner of the antibody. The solid phase support may also be useful as a chromatographic support, such as the carbohydrate polymers Sepharose, Sephadex, or agarose. Indeed, a large number of such supports for binding antibody or antigen are commercially available and known to those having skill in the art.

The binding activity for a given antibody may be determined by well-known methods. Those skilled in the art will be able to determine operative and optimal assay conditions for each determination by employing routine experimentation.

With respect to the anti-cancer antibodies, numerous ways to detectably label such protein molecules are known and practiced in the art. For example, one way the antibodies can be detectably labeled is by linking the antibody to an enzyme, e.g., for use in an enzyme immunoassay (EIA), (Voller et al., 1978, "The Enzyme Linked Immunosorbent Assay (ELISA)", Diagnostic Horizons, 2:1-7; Microbiological Associates Quarterly Publication, Walkersville, Md.; Voller et al., 1978, J. Clin. Pathol., 31:507-520; Butler et al., 1981, Meths. Enzymol., 73:482-523; Enzyme Immunoassay, 1980, (Ed.) Maggio, CRC Press, Boca Raton, Fla.; Enzyme Immunoassay, 1981, (Eds.) E. Ishikawa et al., Kgaku Shoin, Tokyo, Japan). The enzyme that is bound to the antibody reacts with an appropriate substrate, preferably a chromogenic substrate, so as to produce a chemical moiety which can be detected, for example, by spectrophotometric, fluorometric, or by visual detection means. Nonlimiting examples of enzymes which can be used to detectably label the antibodies include malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, ribonuclease, urease, catalase, glucose-6-phosphate dehydrogenase, glucoamylase and acetylcholinesterase. The detection can be accomplished by chromometric methods, which employ a chromogenic substrate for the enzyme, or by visual comparison of the extent of enzymatic reaction of a substrate compared with similarly prepared standards or controls.

A variety of other immunoassays may also be used for detection. For example, by labeling the antibodies, or binding fragments thereof, with a radioisotope, a radioimmunoassay (RIA) can be used to detect cancer-specific antigens (e.g., Colcher et al., 1981, Cancer Research, 41, 1451-1459; Weintraub, "Principles of Radioimmunoassays", Seventh Training Course on Radioligand Techniques, The Endocrine Society, March, 1986). The radioactive isotope label can be detected by using a gamma counter or a scintillation counter or by radiography.

The antibodies, or their antigen-binding fragments can also be labeled using a fluorescent compound. When the fluorescently labeled antibody is exposed to light of the proper wavelength, its presence can then be detected due to fluorescence. Some of the most commonly used fluorescent labeling compounds include fluorescein isothiocyanate, rhodamine, phycoerythrin, phycocyanin, allophycocyanin, o-phthaldehyde and fluorescamine. Detectably labeled fluorescence-emitting metals, such as $^{152}$Eu, or others of the lanthanide series, can be used to label the antibodies, or their binding fragments, for subsequent detection. The metals can be coupled to the antibodies via such metal chelating groups as diethylenetriaminepentacetic acid (DTPA), or ethylenediaminetetraacetic acid (EDTA).

The antibodies can also be detectably labeled by coupling them to a chemiluminescent compound. The presence of the chemiluminescent-tagged antibody is then determined by detecting the presence of luminescence that develops during the course of a chemical reaction. Examples of particularly useful chemiluminescent labeling compounds include, without limitation, luminol, isoluminol, theromatic acridinium ester, imidazole, acridinium salt and oxalate ester. Similarly, a bioluminescent compound may be used to label the antibodies of the present invention. Bioluminescence is a type of chemiluminescence found in biological systems in which a catalytic protein increases the efficiency of the chemiluminescent reaction. The presence of a bioluminescent protein is determined by detecting the presence of luminescence. Useful bioluminescent labeling compounds include luciferin, luciferase and aequorin.

Another embodiment of the present invention provides diagnostics, diagnostic methods and imaging methods for cancers and tumors using the monoclonal antibodies and binding fragments thereof as described by the present invention. The diagnostic uses of the antibodies according to the present invention embrace primary tumors and cancers, as well as metastases. Other cancers and tumors bearing the antigen are also amenable to these diagnostic and imaging procedures.

A diagnostic method according to the invention comprises administering, introducing, or infusing the monoclonal antibodies or their binding fragments as described herein, with or without conjugation to a detectable moiety, such as a radioisotope. After administration or infusion, the antibody or binding fragment binds to the tumor or cancer cells, after which the location of the bound antibodies or fragments is detected. For detectably labeled antibodies or fragments, for example, those labeled with a radioisotope, imaging instrumentation may be used to identify the location of the agent within the body. For unlabeled antibodies or fragments, a second detectable reagent may be administered, which locates the bound antibodies or fragments so that they can be suitable detected. Similar methods have been employed for other antibodies, and the skilled practitioner will be aware of the various methods suitable for imaging the location of detectably bound antibodies or fragments within the body. As a general guidance, about 10-1000 µg, preferably about 50-500 µg, more preferably about 100-300 µg, most preferably about 200-300 µg of Protein G-purified MoAb are administered. For mice, for example, using 200 µg MoAb and intraperitoneal (i.p.) administration, MoAb is injected three times a week for three weeks. For 300 µg MoAb and intraperitoneal (i.p.) administration, MoAb is injected two times a week for three weeks. Applicable doses for humans include about 100-200 mcg/kg, or 350-700 mg/m$^2$.

It is to be further understood that a cocktail of different monoclonal antibodies, such as a mixture of the specific monoclonal antibodies described herein, or their binding fragments, may be administered, if necessary or desired, for cancer treatment. Indeed, using a mixture of monoclonal antibodies, or binding fragments thereof, in a cocktail to target several antigens, or different epitopes, on cancer cells, is an advantageous approach, particularly to prevent evasion of tumor cells and/or cancer cells due to downregulation of one of the antigens.

In another embodiment, the present invention assists in the diagnosis of cancers and tumors by the identification and measurement of the cancer-specific antibody in body fluids, such as blood, serum, plasma, sputum and the like. For those cancers that express the antigen described herein, the ability to detect the antigen provides early diagnosis, thereby affording the opportunity for early treatment. Early detection is especially important for cancers difficult to diagnose in their early stages.

Moreover, the level of antigen detected and measured in a body fluid sample such as blood provides a means for monitoring the course of therapy for the cancer or tumor, including, but not limited to, surgery, chemotherapy, radiation therapy, the therapeutic methods of the present invention, and combinations thereof. By correlating the level of the antigen in the body fluid with the severity of disease, the level of such antigen can be used to indicate successful removal of the primary tumor, cancer, and/or metastases, for example, as well as to indicate and/or monitor the effectiveness of other therapies over time. For example, a decrease in the level of the cancer or tumor-specific antigen over time indicates a reduced tumor burden in the patient. By contrast, no change, or an increase, in the level of antigen over time indicates ineffectiveness of therapy, or the continued growth of the tumor or cancer.

In a related embodiment, the present invention provides methods for diagnosing cancers by assaying for changes of levels in the cancer-specific antigen in cells, tissues or body fluids compared with the levels in cells, tissues, or body fluids, preferably of the same type, from normal human controls. A change, especially an increase, in levels of antigen in the patient versus the normal human control is associated with the presence of cancer. Typically, for a quantitative diagnostic assay, a positive result indicating that the patient being tested has cancer, is one in which levels of the antigen in or on cells, tissues or body fluid are at least two times higher, and preferably three to five times higher, or greater, than the levels of the antigens in or on the same cells, tissues, or body fluid of the normal individual as control. Normal controls include a human without cancer and/or non-cancerous samples from the patient.

Another embodiment of the present invention relates to pharmaceutical compositions comprising one or more monoclonal antibodies, or binding fragments thereof, according to the invention, together with a physiologically- and/or pharmaceutically-acceptable carrier, excipient, or diluent.

More specifically, the present invention is directed to pharmaceutical compositions comprising a monoclonal antibody, or binding fragment thereof, including the monoclonal antibodies produced from the hybridoma cell line 7C8; antibodies that are capable of binding to the same antigenic determinant as do the monoclonal antibodies produced by the hybridoma cell line 7C8; binding fragments thereof, and binding fragments of monoclonal antibody capable of binding to the same antigenic determinant, and a pharmaceutically-acceptable carrier or diluent. Preferably, the pharmaceutical composition comprises monoclonal antibody 7C8.

Preferably, the antibodies or binding fragments thereof are delivered parenterally, such as by intravenous, subcutaneous, or intraperitoneal administration, e.g., injection. Suitable buffers, carriers, and other components known in the art can be used in formulating a composition comprising the antibody or fragments for suitable shelf-life and compatibility for the administration. These substances may include ancillary agents such as buffering agents and protein stabilizing agents (e.g., polysaccharides).

More specifically, therapeutic formulations of the antibodies, or binding fragments thereof, are prepared for storage by mixing the antibodies or their binding fragments, having the desired degree of purity, with optional physiologically acceptable carriers, excipients, or stabilizers (Remington's Pharmaceutical Sciences, 17th edition, (Ed.) A. Osol, Mack Publishing Company, Easton, Pa., 1985), in lyophilized form or in the form of aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 amino acid residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

The antibodies, or binding fragments thereof, also may be entrapped in microcapsules prepared, for example, by coacervation techniques or by interfacial polymerization (for example, hydroxymethylcellulose or gelatin-microcapsules and poly-[methylmethacylate] microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, supra.

Antibodies or their binding fragments to be used for in vivo administration must be sterile. This is readily accomplished by filtration through sterile filtration membranes, prior to or following lyophilization and reconstitution. The antibodies, or binding fragments thereof, ordinarily will be stored in lyophilized form or in solution.

Therapeutic antibody compositions generally are placed into a container having a sterile access port, for example, an intravenous solution bag or vial having a stopper pierceable by a hypodermic injection needle. The route of administration of the antibodies, or binding fragments thereof, in accordance with the present invention, is in accord with known methods, e.g., injection or infusion by intravenous, intraperitoneal, intramuscular, intrarterial, subcutaneous, intralesional routes, by aerosol or intranasal routes, or by sustained release systems as noted below. The antibodies, or binding fragments thereof, are administered continuously by infusion or by bolus injection. Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., 1981, J. Biomed. Mater. Res., 15:167-277 and Langer, 1982, Chem. Tech., 12:98-105), or poly(vinylalcohol)], polylactides (U.S. Pat. No. 3,773,919; EP 58,481), copolymers of L-glutamic acid and gamma ethyl-L-glutamate (Sidman et al., 1983, Biopolymers, 22:547-556), non-degradable ethylene-vinyl acetate (Langer et al., supra), degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid (EP 133, 988).

While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in effectiveness. Rational strategies can be devised for antibody stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release antibody compositions also include liposomally entrapped antibodies, or their binding fragments. Liposomes containing the antibodies are prepared by known methods, for example, DE 3,218,121; Epstein et al., 1985, Proc. Natl. Acad. Sci. USA, 82:3688-3692; Hwang et al., 1980, Proc. Natl. Acad. Sci. USA, 77:4030-4034; EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200-800 Angstroms) unilamellar type in which the lipid content is greater than about 30 mol. % cholesterol, the selected proportion being adjusted for the optimal antibody therapy.

An effective amount of antibody to be employed therapeutically will depend, for example, upon the therapeutic and treatment objectives, the route of administration, the age, condition, and body mass of the patient undergoing treatment or therapy, and auxiliary or adjuvant therapies being provided to the patient. Accordingly, it will be necessary and routine for the practitioner to titer the dosage and modify the route of administration, as required, to obtain the optimal therapeutic effect. A typical daily dosage might range from about 1 mg/kg to up to about 100 mg/kg or more, preferably from about 1 to about 10 mg/kg/day depending on the above-mentioned factors. Typically, the clinician will administer antibody until a dosage is reached that achieves the desired effect. The progress of this therapy is easily monitored by conventional assays.

Various adjuvants may be used to increase the immunological response to the antigen and to elicit specific antibodies according to the present invention. Depending on the host species to be immunized, adjuvants may include, but are not limited to, Freund's (complete and incomplete), mineral gels, such as aluminum hydroxide, surface active agents, such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

The antibodies of the present invention are also useful for in vitro diagnostic applications for the detection of cancer cells that possess the antigen for which the antibodies are specific. As detailed above, in vitro diagnostic methods include immunohistological or immunohistochemical detection of tumor cells (e.g., on human tissue, or on cells dissociated from excised tumor specimens), or serological detection of tumor associated antigens (e.g., in blood samples or other biological fluids). Immunohistochemical techniques involve staining a biological specimen, such as a tissue specimen, with one or more of the antibodies of the invention and then detecting the presence on the specimen of antibody-antigen complexes comprising antibodies bound to the cognate antigen. The formation of such antibody-antigen complexes with the specimen indicates the presence of cancer in the tissue.

Detection of the antibody on the specimen can be accomplished using techniques known in the art such as immunoenzymatic techniques, e.g., immunoperoxidase staining technique, or the avidin-biotin technique, or immunofluorescence techniques (see, e.g., Ciocca et al., 1986, "Immunohistochemical Techniques Using Monoclonal Antibodies", Meth. Enzymol., 121:562-79 and Introduction to Immunology, Ed. Kimball, (2.sup.nd Ed), Macmillan Publishing Company, 1986, pp. 113-117). Serologic diagnostic techniques involve the detection and quantification of tumor-associated antigens that have been secreted or "shed" into the serum or other biological fluids of patients thought to be suffering from, as mentioned above. Such antigens can be detected in the body fluids using techniques known in the art, such as radioimmunoassays (RIA) or enzyme-linked immunoabsorbant assays (ELISA), wherein antibody reactive with the shed antigen is used to detect the presence of the antigen in a fluid sample (See, e.g., Uotila et al., 1981, J. Immunol. Methods, 42:11 and Fayed et al., 1998, Disease Markers, 14:155-160).

In yet a further aspect of the invention, monoclonal antibodies or binding fragments to the antigen are provided labeled with a detectable moiety, such that they may be packaged and used, for example, in kits, to diagnose or identify cells having the aforementioned antigen. The kits preferably contain an instruction manual for use of the kit. Non-limiting examples of such labels include fluorophores such as fluorescein isothiocyanate; chromophores, radionuclides, or enzymes. Such labeled antibodies or binding fragments may be used for the histological localization of the antigen, ELISA, cell sorting, as well as other immunological techniques for detecting or quantifying the antigen, and cells bearing the antigen, for example.

The antibodies of the present invention exhibit cancer or tumor specificity. In this regard, MoAb 7C8 reacts with several human cancer cells, including breast, lung, and bladder cancers, but not with non-cancer cells of the same tissues (see Table 2, infra).

Characterization of the cancer-specific antigens shows that they are detected by MoAb 7C8, but migrate as multiple as a single bands by Western Blot analysis (FIG. 2).

EXAMPLES

The examples as set forth herein are meant to exemplify the various aspects of carrying out the invention and are not intended to limit the invention in any way.

Example 1

Mice were immunized with intact human breast cancer cells. Spleens of immunized mice were fused with HL-1 myeloma cells to generate 1,000 monoclonal hybridoma cultures. Supernatant fluids from these cultures were screened in solid phase EIAs for the presence of immunoglobulin reactive with live breast cancer cell lines and not reactive with live normal human mammary epithelial cells. Whereas many cultures demonstrated immunoglobulin reactive with all test antigens, clone 7C8 contained immunoglobulin reactive only with the breast cancer cells but not the normal epithelial cells.

Upon further study against human cancer tissue arrays by Immunohistochemistry, monoclonal antibody 7C8 was demonstrated to be reactive and bind to 67% of breast cancer, 42% of lung cancer and 92% of bladder cancer, but not reactive and bind to corresponding normal human tissues. Monoclonal antibody 7C8 detected multiple protein bands at about 40-52 and 130-200 kDa in human breast cancer cell line MDA-MB-468 cells. The isotype of 7C8 is IgG1.

Materials and Methods

Breast cancer cells: primary cultures were prepared from breast tumors from patients. Tissues were cut into 2~3 mm pieces and washed in ice-cold PBS before digested with collagenase (10 µg/ml) at 37° C. for 30 minutes. The digested tissues were disrupted into single cell suspension in DMEM (containing 4.5 g/L glucose and 110 mg/L sodium pyruvate and 2 mM L-glutamine) with a 5 ml syringe. The cells were spun down and resuspended in DMEM with 10% FBS (v/v fetal bovine serum) and seeded in tissue culture dishes. After a one-week incubation, the cells were washed with ice-cold PBS and detached by 10 mM EDTA in PBS. The cells were collected for immunization.

Immunizations. Four-week old BABL/c mouse was immunized with 10 millions breast cancer cells, mixed with an equal volume of complete Freund's adjuvant. After a few boosting, the titers of tail bleeds from the immunized mice were tested against live breast cancer cell lines, MDA-MB-468 and MCF-7. Once high titer observed, the spleens were removed for cell fusion with murine myeloma cells. The hybridoma technique described originally by Kohler and Milstein, Eur. J. Immunol. 6, 511 (1976) has been widely applied to produce hybrid call lines that secrete high levels of monoclonal antibodies against many specific antigens.

Hybridoma supernatants were tested for presence of antibodies specific for human breast cancer cell surface specific antigen by ELISA.

For the ELISA, 100,000 cells of either MDA-MB-468, or MCF-7, or MCF-12 were seeded in each well of 96-well culture plates in DMEM plus 10% FBS. After a 24-hr incubation, the cells were washed with PBS three times, then incubated with the hybridoma culture supernatants diluted 1:1 in DMEM with 5% FBS for 1 hour at room temp. Plates were washed again and 0.1 ml per well of an appropriate dilution of goat anti-mouse immunoglobulin coupled to horseradish peroxidase was added. The plates were incubated again for 1 hour at room temperature and then washed as above. Tetramethylbenzidine (TMB) was added as substrate, incubated for 15-20 minutes at room temperature and then the absorbance of each well was then read at 492 nm.

Approximately 150 well supernatants reacted with the targets on the cell surfaces of either one or two, or all three cell lines. Fifty-three (53) hybridomas, including clone 7C8, produced monoclonal antibodies that are human breast cancer specific.

Example 2

Immunohistochemistry of Paraffin Sections with monoclonal antibody 7C8: Place the slide in microwave and heat the slide at power 7 for 3.5 min. Incubate sections in three washes of xylene for 5 min each. Incubate sections in two washes of 100% ethanol for 10 min each. Incubate sections in two washes of 95% ethanol for 10 min each. Wash sections twice in dH$_2$O for 5 min each. Wash sections in PBS for 5 min. For antigen unmasking, incubate the slide in ZBP AgRetriev™ solution pre-warmed at 37° C. for 30 minutes.

An alternative methods for antigen unmasking is to heat sections in 10 mM sodium citrate buffer (pH 6.0) in a microwave oven for 1 min at full power followed by 9 min at medium power. Cool slides for 20 min after antigen unmasking. Wash sections in dH$_2$O three times for 5 min each. Incubate sections in 1% hydrogen peroxide for 10 min. Wash sections in dH$_2$O three times for 5 min each. Wash sections in PBS for 5 min. Block each section with 100-400 μl blocking solution (5 mg/ml of BSA in PBS) for 1 h at room temperature. Remove solution and add 100-400 μl diluted primary antibody to each section (dilute antibody in blocking solution.) Incubate overnight at 4° C. Remove antibody solution and wash sections in PBS three times for 5 min each. Add 100-400 μl second antibody, diluted in blocking solution, to each section. Incubate 30 min at room temperature. If using the ABC avidin/biotin kit (Vector Laboratories, Burlingame, Calif.) the reagent is prepared according to the manufacturer's instructions and the solution is incubated for 30 min at room temperature. Remove ABC reagent and wash sections three times in PBS 5 min each. Add 100-400 μl DAB reagent to each section and monitor staining closely. As soon as the section turns brown, immerse slides in dH$_2$O. Wash sections in dH$_2$O two times for 5 min each. Document the images under microscope.

Example 3

Isotyping of Monoclonal Antibodies: Culture supernatants or purified antibodies were incubated with the isotyping dip stick manufactured by Roche Molecular Diagnostic Inc.

Example 4

Western Blot Analysis: 10 millions of MDA-MB-468 cells were collected in 1 ml of RIPA buffer (50 mM Tris HCI pH 7.4, 1% NP-40, 0.25% sodium deoxycholate, 150 mM NaCl, 1 mM EDTA, 1 mM sodium orthovanadate, 1 mM NaF, protease inhibitors). 0.1 mg of protein from each sample was used for immunoblotting. form of PARP were detected using a mouse monoclonal anti-PARP antibody from Oncogene research. a-Actin was used for normalizing the loading.

Three different human mammary epithelial cells were seeded at 10,000 cells/well of 96-well culture plate. The next day, the live cells were incubated with 1:1 diluted culture supernatants from hybridoma clone 7C8 in 5% BSA in DMEM. MDA-MB-468 cells are estrogen-independent human breast cancer cells. Human breast cancer cell line MCF-7 cells are estrogen-dependent, while MCF-12A cells are normal human mammary epithelial cells. Monoclonal antibody 7C8 reacts to live human breast cancer cell lines MDA-MB-468 and MCF-7 cells but not to normal human mammary epithelial cell line MCF-12. The results are shown in Table 1.

TABLE 1

Immunostaining of Different Breast Epithelial Cells by 7C8

| Clone # | MDA468 | MCF-7B | MCF-12A |
|---|---|---|---|
| 7C8 | 0.279 | 0.139 | 0.032 |

Example 5

Immunochemistry staining of different cancer cells with MoAb 7C8: Fixed sections from various human cancer tissues and normal tissues were stained with 0.5 micro-gram/ml of monoclonal antibody 7C8 following the immunohistochemistry protocol mentioned above. As can be seen from FIG. 1, the monoclonal antibody 7C8 reacted to human cancer tissues specifically, while no reactivity was observed with the normal human tissues.

A human tissue array of 198 fixed-sections from various human cancer tissues or normal tissues were stained with 1 microgram/ml of monoclonal antibody 7C8. As shown in Table 2, monoclonal antibody 7C8 reacted specifically with 67% of breast cancer tissues, 42% of lung cancers and 92% of bladder cancers. No significant staining with normal tissues were observed.

Example 6

Characterization of the cancer-specific antigen via Western blot analysis: 0.1 million cells-equivalent total MDA-MB-468 breast cancer cell lysate was loaded in each lane and Western blot with monoclonal antibody clone 7C8 and other monoclonal antibodies at concentration of 1 microgram/ml. The results are shown in FIG. 2. Monoclonal antibody 7C8 detected multiple bands with an MW of between about 40-52 and 130-200 kDa.

TABLE 2

Summary of Immunohistochemistry of Tissue Array

| Tissue | Cancer | Normal |
|---|---|---|
| Breast | 8/12 | 0/6 |
| Lung | 5/12 | 0/6 |
| Bladder | 11/12 | 0/6 |

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof.

What is claimed is:

1. A monoclonal antibody produced by the hybridoma cell line deposited in the ATCC as patent deposit designation PTA-7448 designated as 7C8, or an antigen-binding fragment thereof, which binds specifically to an antigen present in human breast cancer, human lung cancer, or human bladder cancer.

2. The monoclonal antibody or antigen-binding fragment thereof, according to claim 1, wherein the antigen-binding fragment is selected from the group consisting of Fab fragments, $F(ab)_2$ fragments, Fab' fragments, $F(ab')_2$ fragments, Fd fragments, Fd' fragments and Fv fragments.

3. An anti-idiotypic antibody which mirrors the binding site of the antibody or antigen-binding fragment according to claim 1.

4. A hybridoma cell line which produces a monoclonal antibody, wherein said hybridoma cell line is deposited in the ATCC as patent deposit designation PTA-7448.

5. A method of localizing cancer cells in a patient, comprising: (a) administering to the patient a detectably-labeled monoclonal antibody, or antigen-binding fragment thereof, according to claim 1; (b) allowing the detectably-labeled monoclonal antibody, or antigen-binding fragment thereof, to bind to the cancer cells within the patient; and (c) determining the location of the labeled monoclonal antibody or antigen-binding fragment thereof, within the patient.

6. A method of imaging cancer in a patient, comprising administering to the patient the antibody or antigen-binding fragment thereof according to claim 1, wherein the antibody or antigen-binding fragment thereof is detectably labeled with paramagnetic ions or with a radioisotope.

7. A pharmaceutical composition comprising the monoclonal antibody, or antigen-binding fragment thereof, according to claim 1, and a pharmaceutically acceptable carrier, excipient, or diluent.

8. The monoclonal antibody or antigen-binding fragment thereof according to claim 1, labeled with a detectable moiety.

9. The monoclonal antibody or antigen-binding fragment thereof according to claim 8, wherein the detectable moiety is selected from the group consisting of a fluorophore, a chromophore, a radionuclide, a chemiluminescent agent, a bioluminescent agent and an enzyme.

10. The antibody or antigen-binding fragment thereof of claim 1, wherein the antibody or antigen-binding fragment is humanized or chimerized.

11. A composition comprising the monoclonal antibody or antigen-binding fragment thereof of claim 1.

12. A kit comprising the monoclonal antibody or antigen-binding fragment thereof of claim 1.

* * * * *